US006753971B1

(12) United States Patent
Hertling

(10) Patent No.: US 6,753,971 B1
(45) Date of Patent: Jun. 22, 2004

(54) METHOD FOR DETERMINING GEOMETRIC STRUCTURES ON OR IN A SUBSTRATE AS WELL AS MATERIAL PARAMETERS

(75) Inventor: Rolf Hertling, Aachen (DE)

(73) Assignee: Steag ETA-Optik GmbH (DE)

( * ) Notice: Subject to any disclaimer, the term of this patent is extended or adjusted under 35 U.S.C. 154(b) by 37 days.

(21) Appl. No.: 10/111,134

(22) PCT Filed: Sep. 29, 2000

(86) PCT No.: PCT/EP00/09533

§ 371 (c)(1), (2), (4) Date: Apr. 19, 2002

(87) PCT Pub. No.: WO01/29502

PCT Pub. Date: Apr. 26, 2001

(30) Foreign Application Priority Data

Oct. 20, 1999 (DE) ........................................ 199 50 559

(51) Int. Cl.[7] ................................................ G01B 11/24

(52) U.S. Cl. ....................................... 356/601; 356/613

(58) Field of Search ................................ 356/445, 446, 356/630, 631, 632, 369

(56) References Cited

U.S. PATENT DOCUMENTS 4,555,767 A * 11/1985 Case et al. ............... 250/341.4
4,854,707 A 8/1989 Ring et al.
5,539,213 A 7/1996 Meeks et al.
5,596,406 A * 1/1997 Rosencwaig et al. ....... 356/327
5,604,581 A 2/1997 Liu et al.
5,739,909 A * 4/1998 Blayo et al. ................ 356/369
5,867,276 A * 2/1999 McNeil et al. ............. 356/445
5,963,329 A 10/1999 Conrad et al.

FOREIGN PATENT DOCUMENTS

| | | |
|---|---|---|
| DE | 4228870 | 3/1994 |
| DE | 19739794 | 4/1999 |
| DE | 19852323 | 5/2000 |
| WO | WO 99/45340 | 9/1999 |
| WO | WO 99/56174 | 11/1999 |

OTHER PUBLICATIONS

JP 08329534, Patent Abstracts Of Japan.

JP 1–145504, Patent Abstracts of Japan.

JP 8153214, Patent Abstracts of Japan, Published Jun. 11, 1996.

* cited by examiner

*Primary Examiner*—Hoa Q. Pham
(74) *Attorney, Agent, or Firm*—R W Becker & Associates; R W Becker

(57) ABSTRACT

In order to determine geometric structures and/or material parameters on or in substrates and in a locally resolved manner over the substrate surface, the invention provides the following measures: Measuring reflection and/or transmission light intensity values of the diffracted light according to the wavelength; calculating the reflection and/or transmission light intensity values using an iteration model into which the individual layer-structure and/or material parameters enter, and; modifying the parameters until the measured and calculated values coincide to the greatest possible extent.

13 Claims, 2 Drawing Sheets

2
1
X
A
B
C
D
E

METHOD FOR DETERMINING GEOMETRIC STRUCTURES ON OR IN A SUBSTRATE AS WELL AS MATERIAL PARAMETERS

BACKGROUND OF THE INVENTION

The invention relates to a method of determining geometrical structures on or in a substrate on which diffraction of light occurs, as well as a method of determining parameters of the materials present on or in a substrate, whereby geometrical structures that lead to diffraction of light are present in or on the substrate.

Substrates having structures are, for example, optical storage media (CD, CD-R, DVD, CD-RW, DVD-RW, DVD-R, MO/MD, etc.), which are provided with channels, so-called grooves, for the recording, reading and/or erasing of data, and the geometries of which, such as depth, width and spacing, differ for the various types of media and are manufacturer specific. On the structured substrates, preferably blanks of polycarbonate, where for the manufacture of the optical storage media various layers having different refractive and/or absorption indices, and varying layer thicknesses, are applied, so that the desired optical, thermal, electrical, and mechanical properties of the storage medium result. Methods for the measurement of thicknesses of continuous layers are known and are described, for example, in DE 197 39 794 A, which originates from the same applicant, and in the documents mentioned there, as well as in U.S. Pat. No. 5,963,329. However, with the known method it is not possible to determine the various thicknesses that are present over the substrate surface, in other words, to determine a lateral change in layer thickness perpendicular to the direction of the build-up of the layer.

It is therefore an object of the present invention to provide a method that enables not only the determination of thicknesses of continuous layers, but also of geometrical structures on or in a substrate. It is a further object of the present invention to provide a method for determining parameters of the materials present on or in a substrate.

SUMMARY OF THE INVENTION

The stated object is realized with a method of determining geometrical parameters on or in a substrate, on which diffraction of light occurs, by the following method steps:

- Measuring reflection and/or transmission light intensity values of the diffracted light as a function of the wavelength,
- Calculating the reflection and/or transmission light intensity values using an iteration model in which are incorporated the individual layer, structure and/or material parameters, and
- Modifying the parameters until the measured and calculated values coincide to the greatest extent possible.

In this connection, the layer, structure and/or material parameters vary over the surface of the substrate, are segmented in a lateral direction, and the layer, structure and/or material parameters of the individual segments are determined.

With the inventive method it is possible to measure not only the surface structures, such as grooves or channels, that are present in a substrate, but also the geometrical structures of coatings and layers of various materials that are applied to the substrate. For example, it is possible with the inventive method to also determine segmentations that are present at right angles to the direction of the build-up of a layer, in other words, lateral structures, such as are present, for example, with information-carrying substances of one time writable CD's (CD-R). As a consequence of the inventive measures, by amplitude and/or inphase overlapping of all partial waves to simulate the optical spectra, and by variation of the geometrical parameters to determine these parameters such that the measured and modulated spectra coincide optimally, it is possible to also locally determine layers that are present or applied over the substrate with varying layer thicknesses. Since the spectra react very sensitively to changes of the thicknesses of thin layers, for example in the nanometer range, the precision of the inventive method is accordingly high. The inventive method furthermore operates in a non-destructive manner and without the necessity for preparing samples, as is the case with conventional methods.

Pursuant to the inventive method, in a first method step the reflection and/or transmission light intensity values of the diffracted light are measured as a function of the wavelength. In this connection, it is particularly advantageous to measure the diffracted light of zero order of diffraction, although the diffracted light of higher orders of diffraction can also be evaluated for this measurement.

With the inventive method the determination of the geometrical dimensions of the structures in and/or on the substrate is particularly advantageous. In this connection, the geometrical structures are preferably determined by the thicknesses of the layers applied to the substrate.

Pursuant to a particularly advantageous embodiment of the invention, the local structures on the substrate surface are determined. As a result, it is possible to locally determine lateral segmentations or differences in relief over the surface of the substrate.

For the case where the structures on the substrate continuously vary over the substrate surface it is particularly advantageous pursuant to a further embodiment of the invention if at least these regions of continuously varying structures are segmented by the formation of polygons, and the structures of the individual polygonal segments are determined. In this way, it is also possible with the inventive method to determine, for example, inclined or rounded surface portions by dividing the structures into a resolution of segments or cells, whereby the precision of the determination of the structure is selectable by means of the fineness of the resolution. The structure of such a multi-component sectioning is thus sensed by suitable resolution with cells of any material, thickness, depth and/or width.

The structures that possibly also vary at least partially continuously over the surface of the substrate are preferably formed by layers that are applied to the substrate. In this connection, it is particularly advantageous if the inventive method is utilized for regulating the structure formation in a manufacturing process. This means that the determined data is input into a closed control loop of a production unit for the respective determination or fixing of the adjustment values. The inventive method is thus preferably used "inline" in a manufacturing process.

It is, of course, also possible to use the inventive method for the measurement of structures of substrates and of substrate layers applied thereon, and hence for the determination of the quality of multi-component structures or media, in other words, for the "offline" control.

Pursuant to a particularly advantageous embodiment of the inventive method, the reflection and/or transmission light intensity values of the diffracted light are simulated as a function of the wavelength for the in, formation of desired optical target data. Thus, instead of the measurement of the light intensity values, the inventive method also enables the simulation of desired optical target data and hence the fixing, in other words a structure design, of the structure that is to be applied to a substrate, for example a multi-component system in the case of optical storage media.

Pursuant to one advantageous embodiment of the invention, the substrates are blanks for data storage media, whereby the structures are embodied as channels in the blank, and the structures that are applied to the blank are formed of layers of information-carrying substances, so-called dyes. The layer thicknesses, the so-called segmentations, that vary over the surface of the substrate, result, for example with one-time writable CDs (CD-R), in that the dye-layer thickness in the grooves is greater than the thickness between the grooves, in the so-called land regions, since in the case of this storage media the groove depth is very great, for example in contrast to the groove depth with the CD-RW.

The inventive method is, of course, not limited to use in conjunction with optical storage media and the manufacture thereof. For example, it is also very advantageously possible to use the method in conjunction with the determination of surface factors of other objects, such as, e.g., indicating devices, displays and others.

Furthermore, the present method is also suitable not only for the determination of surface structures, but also of parameters of materials that are present on or in a substrate. This object is inventively realized with a method for the determination of parameters of the materials present on or in a substrate, whereby geometrical structures that lead to diffraction of light are present in or on the substrate, and in particular by the following method steps:

- Measuring reflection and/or transmission light intensity values of the diffracted light as a function of the wavelength,
- Calculating the reflection and/or transmission light intensity values using an iteration model in which are incorporated individual layer, structure and/or material parameters, and
- Modifying the parameters until the measured and calculated values coincide to the greatest possible extent.

In this connection, the layer, structure and/or material parameters vary over the surface of the substrate, are segmented in a lateral direction, and the layer, structure and/or material parameter of the individual segments are determined.

Such a measuring method is again usable in a non-destructive manner and not only in "offline" as well as in "inline", applications in conjunction with optical storage media, but also with other objects, such as, for example, displays and the manufacture thereof.

BRIEF DESCRIPTION OF THE DRAWINGS

The invention, as well as its development and advantages, will be explained subsequently in conjunction with the example of measuring and coating a CD-R with reference to the figures. The drawings show.

DESCRIPTION OF PREFERRED EMBODIMENTS

Figure 1:
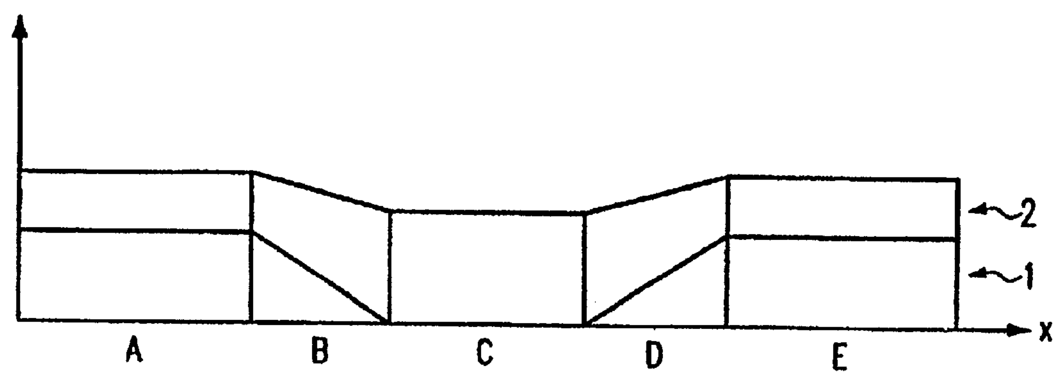
FIG. 1 a schematic cross-sectional view through one portion of a substrate provided with layers for a CD-R, FIG. 2 a graph in which the reflection-light intensity values are plotted against the wavelength, FIG. 3 an example for the determination of locally resolved dimensions of the structure in the region of the groove, and FIG. 4 an example for the determination of the locally resolved dimensions of the structure in the land region.

In FIG. 1, plotted on the x-axis are the lateral dimensions of a cross-sectional portion through a CD-R, which lateral dimensions extend in the x-y plane, and plotted on the Z-axis, in the vertical direction, are the layer thicknesses.

The blank 1, which in the present embodiment is fabricated from polycarbonate, is provided in the first lateral segmental region A with a so-called land region, which in the lateral segmental region D continuously drops into a so-called groove region C, which then merges in the x-direction in a further transition region D to the land region E, which corresponds to the land region A. Thus, the blank 1 is embodied with a groove or channel C, and its transition regions B, D merge into the land regions A, E.

Applied onto this blank 1 is a layer, a so-called dye layer 2. In the land regions A, E this layer is thinner than in the groove region C, whereby the thickness of the layer increases in the transition regions B, D from the groove region C to the land region A, E. Consequently, there results for the dye layer 2 a structure that differs in the lateral direction x, and in particular as a greater thickness yet lower overall height in the groove region C and greater overall dimensions in the land region A, E.

Continuously varying structures, for example the transition regions B, D, are preferably sensed with the inventive method by splitting these regions into segments and polygonizing them (making a traverse survey). The individual segments, and their thicknesses, are then subjected in an appropriate manner to the inventive method. The precision of determining the structure of such transition regions B, D can be controlled by the selection of the degree of fineness of the segmenting and polygonizing.

Figure 2:
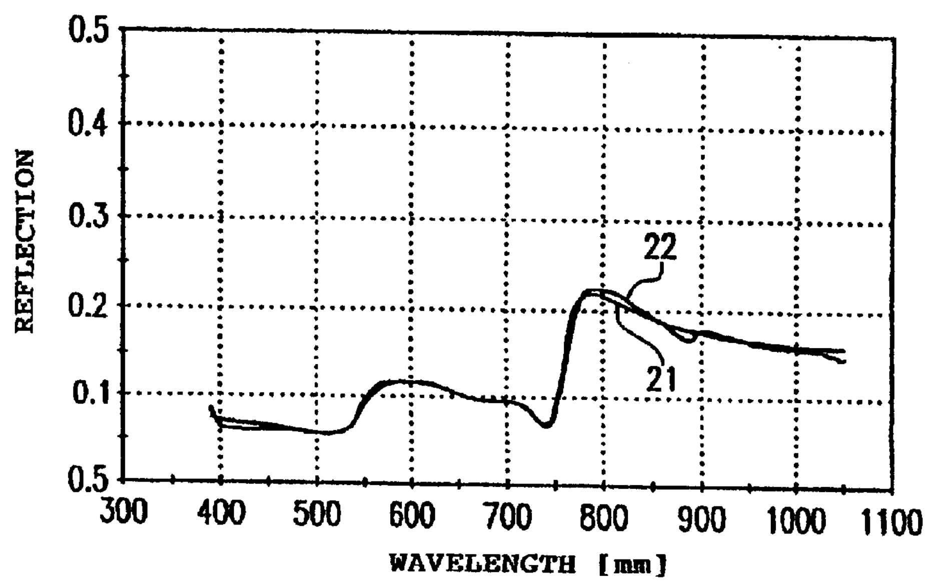

FIG. 2 illustrates a curve 21 for the calculated reflectivity, and a curve 22 for the measured reflectivity plotted with respect to wavelength. The reflectivity of the curve 21 is calculated from initially prescribed optical models. In accordance therewith, with each calculation step, dimensions of the segmental regions and the layer thicknesses and/or the spectral material parameters, such as, for example, the refraction index n and/or the absorption index k, are varied until a curve 21 results that has as little deviation as possible from the curve 22. From this there then results the parameters of the examined structures, such as the depth, the width and/or the spacing of the substrate and layer structures. In order to this extent to avoid repetition, reference is made to DE 198 52 323 A1, which originates from the same applicant and is not pre-published, and which, to avoid repetition, is incorporated into the present application to the extent that it is pertinent.

Figure 3:
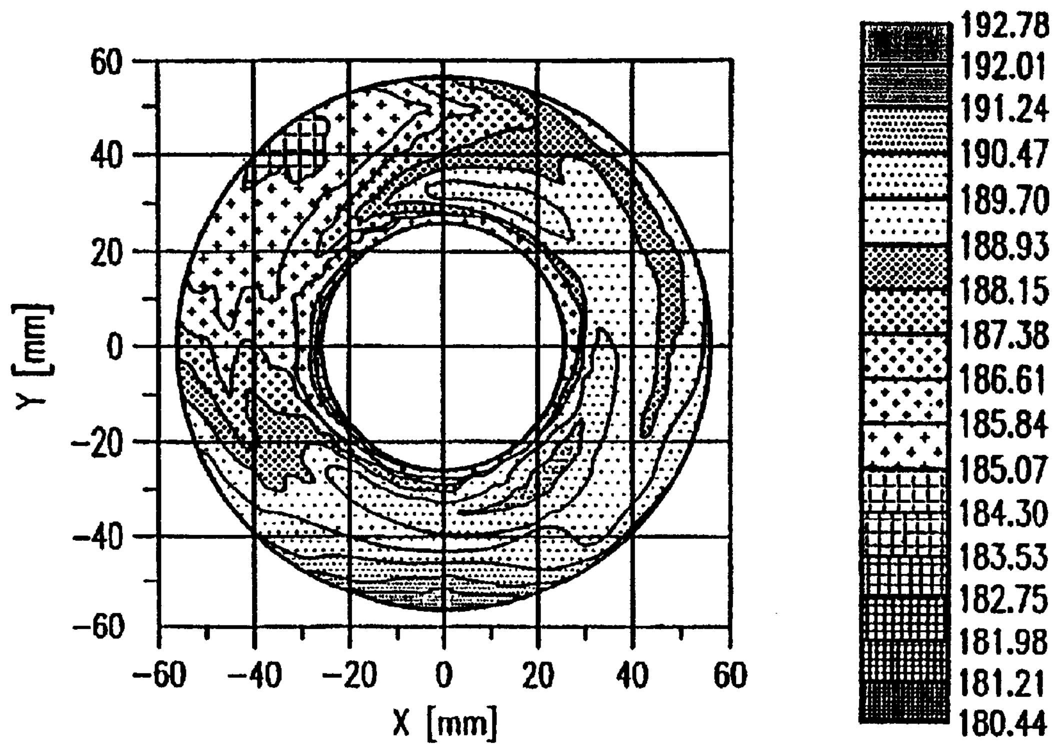
Figure 4:
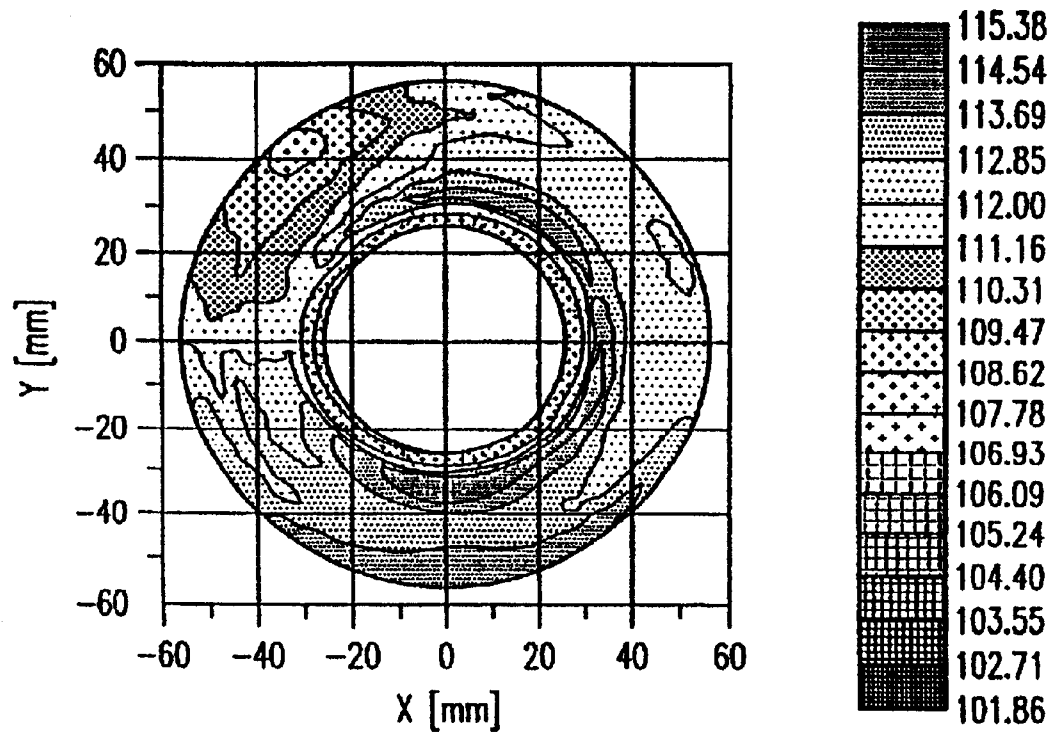

In this connection, the determination of the substrate and layer structure is carried out over the surface of the substrate in a point-by-point manner or in sections and in a lateral direction, so that a measurement of the structures in the lateral direction, for example in the x and y direction, also results in a locally resolved manner, as this can be seen from FIGS. 3 and 4 for segments having differing structural dimensions in the groove region and in the land region over the surface of the substrate. FIGS. 3 and 4 respectively indicate the dye thicknesses in nanometers (nm) for the gradations or shades of color and gray.

The invention was previously explained in conjunction with a very simple embodiment, according to which merely one layer was applied to the substrate. However, the inventive method is also usable with objects and their fabrication where a plurality of layers, layer thicknesses and lateral segmentations are provided, whereby geometrical parameters can also have the value of zero. The geometrical parameters, for example the structures, can in this connection occur not only periodically, as is the case for the grooves of optical storage media, but also non-periodically, and can vary not only in the x direction but also in particular in the y direction, as is the case, for example, with objects having structures that are irregular in the x and y direction, for example with displays.

The specification incorporates by reference the disclosure of German priority document 199 50 559.4 filed 20 Oct. 1999 and International priority document PCT/EP00/09533 filed 29 Sep. 2000.

The present invention is, of course, in no way restricted to the specific disclosure of the specification and drawings, but also encompasses any modifications within the scope of the appended claims.

What is claimed is:

1. A method of determining geometrical structures on or in a substrate on which diffraction of light occurs, said method including the steps of:

measuring at least one of reflection and transmission light intensity values of diffracted light as a function of wavelength;

calculating at least one of reflection and transmission light intensity values using an iteration model in which are incorporated individual parameters of at least one of layer, structure and material; and modifying said parameters until the measured and calculated values coincide to the greatest possible extent, wherein said parameters vary continuously over a substrate surface and are segmented in a lateral direction across the substrate surface by the formation of polygons, and wherein the parameters of individual polygons are determined.

2. A method according to claim 1, wherein said reflection and transmission light intensity values are of zero or higher order of diffraction of said diffracted light.

3. A method according to claim 1, wherein thicknesses of layers applied to a substrate are determined.

4. A method according to claim 1, wherein structures on a substrate surface are determined in a locally resolved manner.

5. A method according to claim 1, wherein the structures are formed by layers applied to a substrate.

6. A method according to claim 1, wherein said method is used for regulating the formation of structures in a manufacturing process.

7. A method according to claim 1, wherein said reflection and transmission light intensity values are simulated for formation of desired optical target data.

8. A method according to claim 7, wherein said method is used to fix or establish a structure in or on a substrate.

9. A method according to claim 1, wherein said substrates are blanks for data storage media.

10. A method according to claim 9, wherein said structures are embodied as channels in said blanks.

11. A method according to claim 9, wherein structures are formed on said blanks by applying information-storage layers.

12. A method according to claim 1, wherein said substrate is a display.

13. A method of determining parameters of materials present on or in a substrate, wherein geometrical structures that lead to diffraction of light are present on or in said substrate, said method including the steps of:

measuring at least one of reflection and transmission light intensity values of diffracted light as a function of wavelength;

calculating at least one of reflection and transmission light intensity values using an iteration model in which are incorporated individual parameters of at least one of layer, structure and material; and modifying said parameters until the measured and calculated values coincide to the greatest possible extent, wherein said parameters vary continuously over a substrate surface and are segmented in a lateral direction across the substrate surface by the formation of polygons, and wherein the parameters of individual polygons are determined.

* * * * *